US010898349B2

(12) United States Patent
Schimmels et al.

(10) Patent No.: US 10,898,349 B2
(45) Date of Patent: Jan. 26, 2021

(54) PASSIVE ANKLE PROSTHESIS WITH ENERGY RETURN

(71) Applicant: Marquette University, Milwaukee, WI (US)

(72) Inventors: Joseph M. Schimmels, Milwaukee, WI (US); Alexander Folz, Milwaukee, WI (US); ShuGuang Huang, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 102 days.

(21) Appl. No.: 16/092,668

(22) PCT Filed: Apr. 14, 2017

(86) PCT No.: PCT/US2017/027577
§ 371 (c)(1),
(2) Date: Oct. 10, 2018

(87) PCT Pub. No.: WO2017/180970
PCT Pub. Date: Oct. 19, 2017

(65) Prior Publication Data
US 2019/0175364 A1    Jun. 13, 2019

Related U.S. Application Data

(60) Provisional application No. 62/322,524, filed on Apr. 14, 2016.

(51) Int. Cl.
*A61F 2/66* (2006.01)
*A61B 17/32* (2006.01)
(Continued)

(52) U.S. Cl.
CPC ...... *A61F 2/6607* (2013.01); *A61B 17/32002* (2013.01); *A61F 2/66* (2013.01);
(Continued)

(58) Field of Classification Search
CPC ... A61F 2/66; A61F 2/6607; A61F 2002/6657
See application file for complete search history.

(56) References Cited

U.S. PATENT DOCUMENTS 6,436,149 B1 *   8/2002   Rincoe ................ A61F 2/6607
                                                               623/47
8,721,737 B2 *   5/2014   Schimmels ........... A61F 2/6607
                                                               623/52
(Continued)

OTHER PUBLICATIONS

International Search Report and Written Opinion in corresponding PCT Application No. PCT/US2017/027577 dated Aug. 17, 2017.

*Primary Examiner* — Bruce E Snow
(74) *Attorney, Agent, or Firm* — Andrus Intellectual Property Law, LLP (57) ABSTRACT

An ankle prosthesis comprises a foot prosthesis. A lower ankle is pivotably secured to the foot prosthesis at an ankle joint. An upper ankle is connected to the lower ankle in a manner that permits vertical movement of the upper ankle relative to the lower ankle. A coupling spring is biased in an extended condition. The coupling spring is connected at a first end to the upper ankle. A second end of the coupling spring is movable in a first condition which is engaged to the lower ankle and in a second condition engaged to the foot prosthesis. Energy is stored in compression of the coupling spring when the coupling spring is in the first condition and energy is released from the coupling spring when the coupling spring is in the second condition.

17 Claims, 8 Drawing Sheets

(51) Int. Cl.
  *A61F 2/68*  (2006.01)
  *A61B 17/00*  (2006.01)
  *A61F 2/50*  (2006.01)

(52) U.S. Cl.
  CPC ........ *A61F 2/68* (2013.01); *A61B 2017/0088* (2013.01); *A61B 2017/00845* (2013.01); *A61F 2002/5018* (2013.01); *A61F 2002/5073* (2013.01); *A61F 2002/6614* (2013.01)

(56) References Cited

U.S. PATENT DOCUMENTS

| | | |
|---|---|---|
| 9,532,877 B2 * | 1/2017 | Holgate .................... A61F 2/66 |
| 2004/0064195 A1 | 4/2004 | Herr |
| 2005/0071018 A1 * | 3/2005 | Phillips .................... A61F 2/66 623/52 |
| 2007/0162152 A1 | 7/2007 | Herr et al. |
| 2010/0114329 A1 | 5/2010 | Casler et al. |
| 2020/0085596 A1 * | 3/2020 | Penot ....................... A61F 2/66 |

* cited by examiner

PASSIVE ANKLE PROSTHESIS WITH ENERGY RETURN

CROSS REFERENCE TO RELATED APPLICATION

This application is the U.S. national stage application of International Application PCT/US2017/027577, filed Apr. 14, 2017, which international application was published on Oct. 19, 2017, as International Publication WO2017/180970 in the English language. The international application is incorporated herein by reference, in entirety. The international application claims priority to U.S. Provisional Patent Application No. 62/322,524, filed on Apr. 14, 2016, the contents of which is hereby incorporated herein by reference in its entirety.

STATEMENT REGARDING FEDERALLY SPONSORED RESEARCH OR DEVELOPMENT

This invention was made with government support under H133G120256-13 awarded by the National Institutes of Health. The government has certain rights in the invention.

BACKGROUND

The field of the invention relates to ankle, foot, and lower leg prosthetic devices. In particular, the field of the invention relates to passive ankle, foot, and lower leg prosthetic devices.

Prosthetic ankle and foot devices have been described. (See U.S. Pat. Nos. 8,721,737; 7,955,399; 7,862,622; 7,819,926; 7,648,533; 7,611,543; 7,578,852; 7,101,403; 6,942,704; 6,929,665; 6,436,149; 6,280,479; 6,206,934; 6,071,313; 5,913,901; 5,728,175; 5,593,455; 5,571,212; 5,509,936; 5,486,209; 5,425,781; 5,425,780; 5,405,411; 5,181,932; 5,156,630; 5,066,305; 4,764,172; 4,645,509; 4,605,417; 4,547,913; 4,442,554; and 4,370,761; and U.S. Published Patent Application Nos. 20110257764; 20110106274; 20090319055; 20090281638; 20090265018; 20080281436; 20080262635; 20080228288; 20080188950; 20080033579; 20070299544; 20070219643; 20070213841; 20070061016; 20060178754; 20060064176; 20050267601; 20050203640; 20050049721; 20050038525; 20050033451; 20050033450; 20040236435; 20040225375; 20040186590; 20030105531; and 20020143407; the contents of which are incorporated herein by reference in their entireties).

An estimated 623,000 are living with a major lower leg amputation (defined as any lower limb amputation greater than the amputation of toes) in the United States. Of these amputations, 78% were due to peripheral vascular disease (PVD) and 45% were due to PVD in individuals with type I or II diabetes. With diabetes and PVD incidence levels on the rise and those in a depressed socio-economic situation more susceptible to develop type II diabetes, the demand for affordable, high quality lower limb prostheses has never been higher. Prostheses currently available on the market include both passive and active devices, neither of which fully satisfies user requirements.

Current commercially available passive prosthetic ankles/feet are based on leaf springs that absorb and release energy during walking. These springs reduce the impact of ground reaction forces that occur during walking and convert some of the absorbed energy into energy used to propel the body forward. The energy stored, however, is significantly less than that is normally required to propel the body forward during push-off in unimpaired walking Amputees that use these existing passive devices tend to walk more slowly and expend more energy than normal walkers. To obtain the desired mechanical characteristics, the ankle joint must display active properties. More energy must be extracted from the ankle than was provided in ankle deflection.

Passive prosthetic ankles, the more commonly prescribed style, are economically priced but lack the powered push-off observed in a natural ankle due to the absence of an actuator. As a result, passive prostheses cause a multitude of quality of life detriments to the end user including asymmetrical gait (for unilateral amputees), slower self-selected walking speeds, higher metabolic cost per distance traveled and increased pain in the residual limb.

Active ankles that were previously being developed at university labs are now being commercialized. The BiOM™ by BionX and the Odyssey™ and Jackspring™ by Spring-Active are now in the relatively early stages of commercialization. These former research prosthetic ankle designs address the need for more energy during push-off to propel the body forward. The limitations of these active (or bionic) designs are the increased size, weight, and cost of the ankle. The degree to which size and weight increases is roughly determined by the amount of power provided by the actuator to propel the body forward. In order to minimize the increased size and weight, a good prosthesis design is one for which the majority of the desired behavior is obtained using passive elements and only a limited contribution is required of the motors.

A review of the different types of ankle prosthesis can be found at the website for the Online Learning Center for the American Academy of Orthotists & Prosthetists, Section 3: Human Foot and Ankle Versus Prosthetic Foot/Ankle Mechanism Function, the content of which is incorporated herein by reference in its entirety. (See also, U.S. Published Application No. 2007/0061016; "SPARKy 3: Design of an active robotic ankle prosthesis with two actuated degrees of freedom using regenerative kinetics", Bellman, R. D., Holgate, M. A., Sugar, T. G., Proceedings of the $2^{nd}$ Biennial IEEE/RAS-EMBS International Conference on Biomedical Robotics and Biomechatronics, 2008; and "Powered Ankle-Foot Prosthesis", Au, S. K., Herr, H. M., IEEE Robotics and Automation Magazine. Vol. 15(3) (pp 52-59), 2008; the contents of which are incorporated herein by reference in their entireties.

As such, new designs for passive prosthetic ankles/feet are desirable, particularly new designs that exhibit energy return that increases with increased walking speed. Also particularly desirable are new designs for passive prosthetic ankles/feet that do not need sensors or actuators to achieve the active behavior associated with normal walking.

BRIEF DISCLOSURE

Disclosed are lower limb prosthetic devices comprising at least a two degree of freedom mechanism. Exemplary devices include a network of conventional springs and elastic beams. In the disclosed devices, the energy stored along one degree of freedom (e.g., energy generated by the weight of the amputee) is released along a different degree-of-freedom to achieve mechanical characteristics similar to that of a natural ankle. As such, the ankle is capable of demonstrating "active behavior," in which more energy is released at the ankle joint than that stored in ankle deflection alone. The energy stored in leg deflection is added to the energy stored in ankle deflection. This total energy is then released at the ankle during push-off.

Other than a related device described in U.S. Pat. No. 8,721,737, active behavior using only passive components had previously not been achieved in a prosthetic ankle design. Prior passive designs do not match natural ankle mechanical characteristics, and prior active designs require large, heavy actuators to achieve similar mechanical characteristics. The devices disclosed herein typically do not need sensors or actuators to achieve the active behavior associated with normal walking.

The devices disclosed herein build upon earlier work of the inventors as disclosed in U.S. Pat. No. 8,721,737, which is incorporated by reference herein in its entirety and describes how energy stored due to deflection along the leg may be used for push-off at the ankle.

The devices as described herein allow deflection along the leg and energy storage to occur at heel strike (i.e., as the foot hits the ground). Energy is stored in a spring and then later released after the ankle has achieved maximum dorsiflexion for well-timed push-off. An additional improvement found in embodiments of the design disclosed herein is that the amount of energy provided during push-off is related to the speed of the walker. This relationship between walking speed and energy generated at the ankle has recently been documented in the analysis of normal healthy walkers. Embodiments as disclosed herein provide a passive ankle device capable of mimicking several key aspects of a natural ankle joint, exemplarily non-linear rotational stiffness and rotational work output (e.g. powered push-off) that increases with walking velocity.

An exemplary embodiment of an ankle prosthesis includes a foot prosthesis. A lower ankle is pivotably secured to the foot prosthesis at an ankle joint. An upper ankle is connected to the lower ankle in a manner that permits vertical movement of the upper ankle relative to the lower ankle. A coupling spring is biased in an extended condition. The coupling spring is connected at a first end to the upper ankle. A second end of the coupling spring is movable between a first condition engaged to the lower ankle and a second condition engaged to the foot prosthesis. Energy is stored in compression of the coupling spring when the coupling spring is in the first condition. Energy is released from the coupling spring when the coupling spring is in the second condition.

In a further exemplary embodiment, the upper ankle includes a ball spline telescopically movable within the lower ankle. The ankle prosthesis exemplarily also includes at least one sprag movably secured to the lower ankle. The at least one sprag is engagable with the ball spline. Operable engagement of the at least one sprag with the ball spline permits movement of the upper ankle towards the lower ankle. Operable engagement of the at least one sprag with the ball spline further prevents movement of the upper ankle away from the lower ankle. In an exemplary embodiment, the ankle prosthesis further includes a sprag release spring secured at a first end to the lower ankle. A second end of the sprag release spring is selectively engaged with the upper ankle such that, when the second end of the sprag release spring is engaged with the upper ankle, translation of the upper ankle towards the lower ankle stores energy in compression of the sprag release spring. In the exemplary embodiment at least one sprag wire is secured between the second end of the sprag release spring and the at least one sprag. Disengagement between the second end of the sprag release spring and the upper ankle imparts a rotative force on the at least one sprag through the at least one sprag wire to disengage the at least one sprag from the ball spline of the upper ankle.

In a further exemplary embodiment, the lower ankle includes a ledge. A block is located at the second end of the coupling spring. The block engages the ledge of the lower ankle when the coupling spring is in the first condition. A jamming mechanism is connected to the block. The jamming mechanism engages the foot prosthesis to move the block from engagement with the ledge of the lower ankle in the first condition of the coupling spring to engagement with the foot prosthesis in the second condition of the coupling spring.

In a further exemplary embodiment the ankle prosthesis includes a dorsiflexion contactor secured to the lower ankle. A dorsiflexion flexure is secured to the foot prosthesis. The dorsiflexion contactor is configured to selectively engage a displacement end of the dorsiflexion flexure to store energy in the dorsiflexion flexure from rotation decreasing an angle between the foot prosthesis and the lower ankle about the ankle joint.

In a further exemplary embodiment, the ankle prosthesis includes a plantarflexion contactor secured to the lower ankle. A plantarflexion flexure is secured to the foot prosthesis. The plantarflexion contactor is configured to selectively engage a displacement end of the plantarflexion flexure to store energy in the plantarflexion flexure from rotation increasing an angle between the foot prosthesis and the lower ankle about the ankle joint.

In a further exemplary embodiment, the ankle prosthesis is a passive ankle prosthesis in which the returned energy increases with walking speed of the patient. In an exemplary embodiment, energy is passively returned using the ankle prosthesis. In an exemplary embodiment of a method of passive energy return, the coupling spring is operated in a first condition with the second end of the coupling spring engaged with the lower ankle. A translational force is received on the upper ankle. Energy is stored in compression of the coupling spring. The coupling spring is operated in the second condition with the second end of the coupling spring engaged with the foot prosthesis. Energy stored in the coupling spring is released to aid rotation of the foot prosthesis relative to the upper ankle about the ankle joint.

DETAILED DISCLOSURE

Unless otherwise specified or indicated by context, the terms "a," "an," and "the," mean "one or more." For example, "a mechanism" should be interpreted to mean "one or more mechanisms."

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

Figure 1:
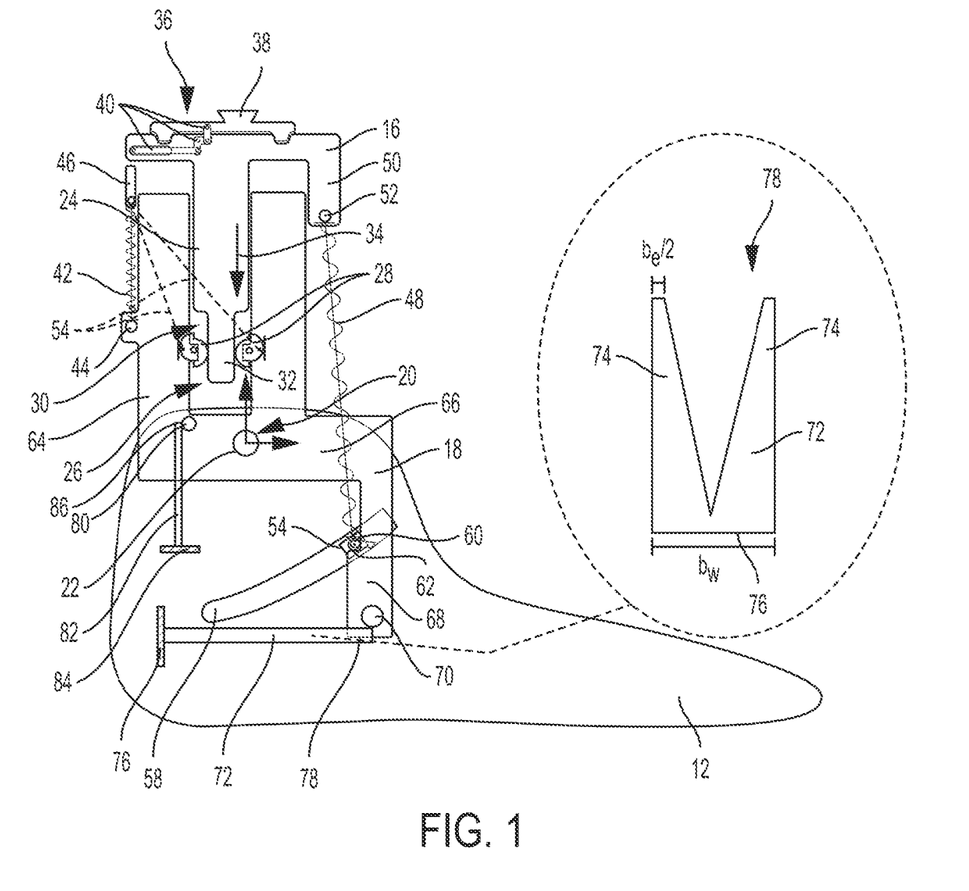
FIG. 1 is a schematic diagram of an exemplary embodiment of a passive ankle prosthesis.
Figure 4:
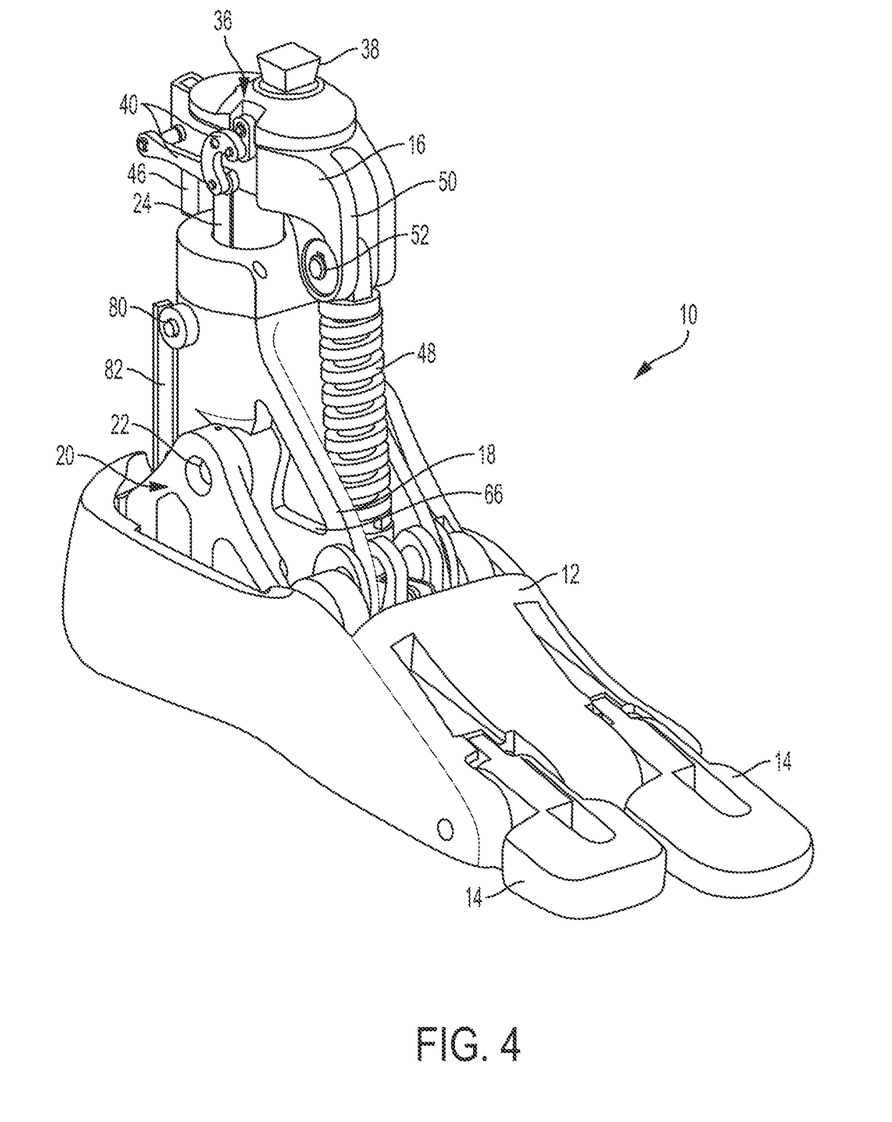
FIG. 4 is a perspective view of an exemplary embodiment of the passive ankle prosthesis.

FIG. 1 is a schematic diagram of an exemplary embodiment of a passive ankle prosthesis 10. FIG. 4 also provides a perspective view of an exemplary embodiment of a passive ankle prosthesis 10. The passive ankle prosthesis 10 includes a foot prosthesis 12. The foot prosthesis 12 includes a resilient material particularly a resilient material located at the bottom of the foot prosthesis 12. As depicted in FIG. 4, an exemplary embodiment of the passive ankle prosthesis 10 may further include one or more toe prosthesis 14 pivotably connected to the foot prosthesis 12; however, it will be recognized that other forms of toe prosthesis may be used or other embodiments may have toe prosthesis which are immobile and an integral part of the foot prosthesis 12.

The passive ankle prosthesis 10 further includes an upper ankle 16 and a lower ankle 18. The lower ankle 18 is pivotably connected to the foot prosthesis 12 at an ankle joint 20. The ankle joint 20 exemplarily includes a pivot pin 22 about which the lower ankle 18 and the foot prosthesis 12 may rotate with respect to one another.

The upper ankle 16 is translationally moveable with respect to the lower ankle 18. A ball spline shaft 24 extends from the upper ankle 16 and is received within a spline chamber 26 defined within the lower ankle 18. A pair of sprags 28 are pivotably secured to the lower ankle 18 within the spline chamber 26 and form a jamming mechanism 30 with a tongue 32 of the ball spline shaft 24. The sprags operate as mechanical diodes, which, as explained in further detail herein permit the upper ankle 16 when loaded, to translate in the direction of arrow 34 relative to the lower ankle 18, while the sprags 28 resist or prevent movement of the upper ankle 16 in the opposite direction until the passive ankle prosthesis 10 is unloaded and mechanically reset. The upper ankle 16 further includes a sprag release mechanism 36. The sprag release mechanism 36 includes a pyramid adapter 38 which facilitates mechanical connection between the passive ankle prosthesis 10 and the residual lower limb of the amputee patient. Mechanical links 40 of the sprag release mechanism 36 connect the pyramid adaptor 38 to the upper ankle 16. A sprag release spring 42 is secured to the lower ankle 18 at connection point 44 and is biased in an extended position. The sprag release spring 42 terminates at an end opposite the connection point 44 at a spring adapter 46. The spring adapter 46, as described in further detail herein, is selectively engaged by a link 40 of the sprag release mechanism 36.

A coupling spring 48 is secured between a coupling arm 50 of the upper ankle 16, and moveably connected to the coupling arm 50 at a connection point 52. The coupling spring 48 is exemplarily biased in an extended configuration. A lower end of the coupling spring 48 is secured to a movable block 54 which is movably held within a channel 58 in the foot prosthesis 12. The block 54 includes a jamming mechanism 60 which operates in the manner as described herein to releasably lock the lower end of the coupling spring 48 in a position relative to the foot prosthesis 12. The block 54 is movably retained on a ledge 62 of the lower ankle 18.

The lower ankle 18 exemplarily includes an upper portion 64 which defines the spline chamber 26. The lower ankle 18 further includes an ankle portion 66 through which the pivot pin 22 extends to define the ankle joint 20. The lower ankle 18 further includes a lower portion 68 which comprises the ledge 62. A dorsiflexion contactor 70 is located on the lower portion 68. The dorsiflexion contactor 70 engages an end of a dorsiflexion flexure 72 of the foot prosthesis 12. In an exemplary embodiment, the dorsiflexion flexure is bifurcated as exemplarily depicted in the inset of FIG. 1. The dorsiflexion flexure 72 may exemplarily comprise two projections 74. The projections 74 may taper in width as depicted as the dorsiflexion flexure 72 extends from a fixed end 76, secured to the foot prosthesis 12 to a displacement end 78. It will be recognized that in embodiments, the lower portion 68 of the lower ankle 18 may comprise two or more dorsiflexion contactors 70 such as to exemplarily engage each of the projections 74 of the dorsiflexion flexure 72.

The lower ankle 18 further includes a plantarflexion contactor 80. The plantarflexion contactor is configured to selectively engage a plantarflexion flexure 82 which extends from a fixed end 84 to a displacement end 86. The fixed end 84 is secured to the foot prosthesis 12. The plantarflexion contactor 80 may be configured to selectively engage the plantarflexion flexure 82 at the displacement end 86 of the plantarflexion flexure. As with the dorsiflexion contactor 70, in embodiments, the lower ankle 18 may include one plantarflexion contactor 80 or more than one plantarflexion contactor 80. Multiple plantarflexion contactors may exemplarily be used to distribute the engagement between the lower ankle 18 and the plantarflexion flexure 82. In an exemplary embodiment, the lower ankle 18 may comprise two or more plantarflexion contactors 80, exemplarily one on either side of the lower ankle 18. Such plantarflexion contactors 80 may correspond to a similar number and oriented plantarflexion flexures 82 of the foot prosthesis 12.

Figure 2:
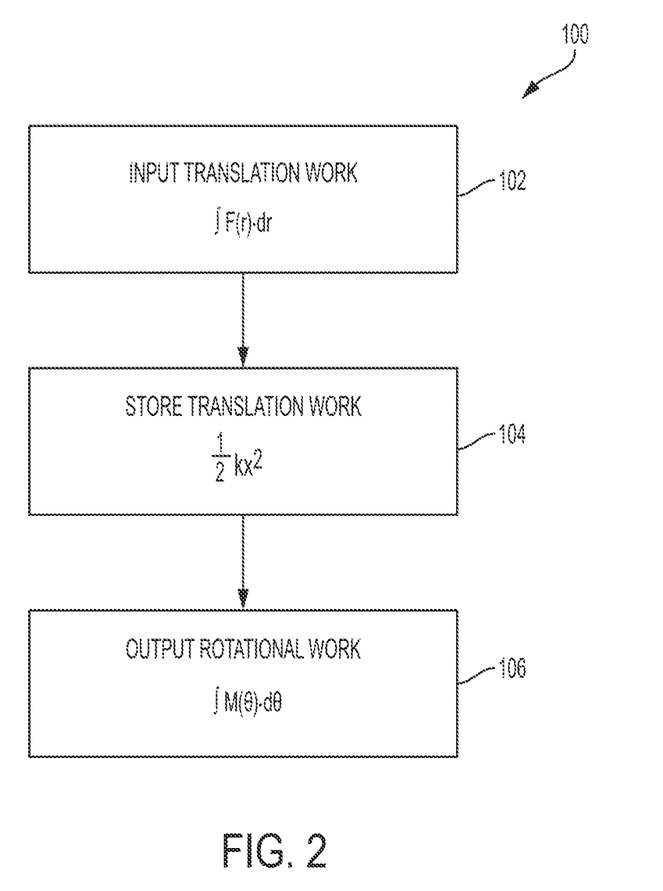
FIG. 2 is a flow chart of an exemplary embodiment of operation of a passive ankle prosthesis.

FIG. 2 is a flow chart that depicts an exemplary embodiment of a method 100 of conversion of work in a passive ankle prosthesis. Carrying out the method 100 may exemplarily occur using embodiments of the passive ankle prosthesis 10 as described above and as exemplarily as described in further detail herein. Embodiments of the method operate to use two compliantly coupled degrees of freedom to achieve powered push off in a manner wherein energy return increases within increasing walking velocity.

At 102 an input of translation work is received. As will be described in further detail herein, a passive ankle prosthesis uses translational work as produced by force along the leg (F) which imparts a deflection along the leg (r). The input of translation work is exemplarily provided by the equation:

$$\int F(r) \cdot dr \qquad (1)$$

Next at 104, the method continues when an embodiment of a passive ankle prosthesis then stores the input translational work in a translational spring with a spring constant (k) and a deflection (x), where x is a function of r. This is exemplarily expressed by the equation:

$$\frac{1}{2}kx^2 \qquad (2)$$

To achieve a power push-off in a passive ankle prosthesis design, the stored energy is converted to rotational work about the ankle joint and output as rotational work at 106. This is exemplarily shown by the equation:

$$\int M(\theta) \cdot d\theta \qquad (3)$$

Where the output rotational work is an integral of the moment (M) about the ankle joint through angle θ. In embodiments of the method 100, and in exemplary operation of embodiments of the passive ankle prosthesis 10, translational energy is stored at the maximum of leg force, early in the stance phase. The passive ankle prosthesis converts that translational energy into rotational work at the maximum dorsiflexion of the prosthesis. Early stance storage and increased work output are achieved, respectively, for example due to the maximum value F which occurs early in the stance phase. The maximum value of F increases with walking velocity, thus in embodiments disclosed herein, the translational energy stored, and the rotational work output increase with an increase in walking velocity.

FIGS. 3A-F functionally depict the operation of the passive ankle prosthesis 10 and also depict an exemplarily embodiment carrying out the method 100 of FIG. 2. It will be recognized that structures and functions as described above, particularly with respect to FIG. 1 similarly apply to FIGS. 3A-F and that for the sake of simplicity, each Figure may not include all of the reference numerals identifying features of the passive ankle prosthesis 10 depicted therein.

Figure 3A:
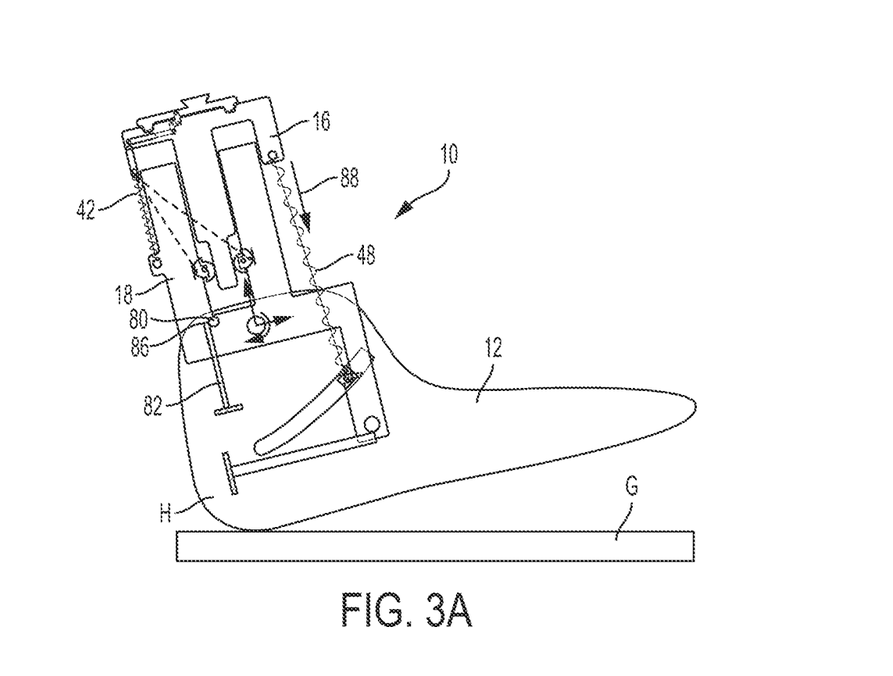
FIGS. 3A-F depict exemplary functional states of a passive ankle prosthesis during operation.

By way of reference, FIG. 1 depicts the functional components of the exemplary embodiment of the passive ankle prosthesis 10 in a neutral or unloaded position. FIGS. 3A-F depict the function of the passive ankle prosthesis 10 through the physiological states of the gait cycle. FIG. 3A exemplarily depicts the passive ankle prosthesis 10 at heel strike. At heel strike, the foot prosthesis 12 contacts the ground G, specifically at the heel H of the foot prosthesis 12. Contact of the foot prosthesis 12 with the ground G causes the translational force of the patient to be transferred to the upper ankle 16 and compress the coupling spring 48 and the sprag release spring 42 in the direction of arrow 88. The upper ankle 16 also moves in the direction of arrow 88 relative to the lower ankle 18. As the foot prosthesis 12 continues to move into full contact with the ground G, the plantarflexion contactor 80 engages the plantarflexion flexure 82, displacing the displacement end 86 of the plantarflexion flexure 82. In this manner, in the course of heel strike, the translation force in the direction of arrow 88 is stored in the sprag release spring 42, coupling spring 48, and the plantarflexion flexure 82.

Figure 3B:
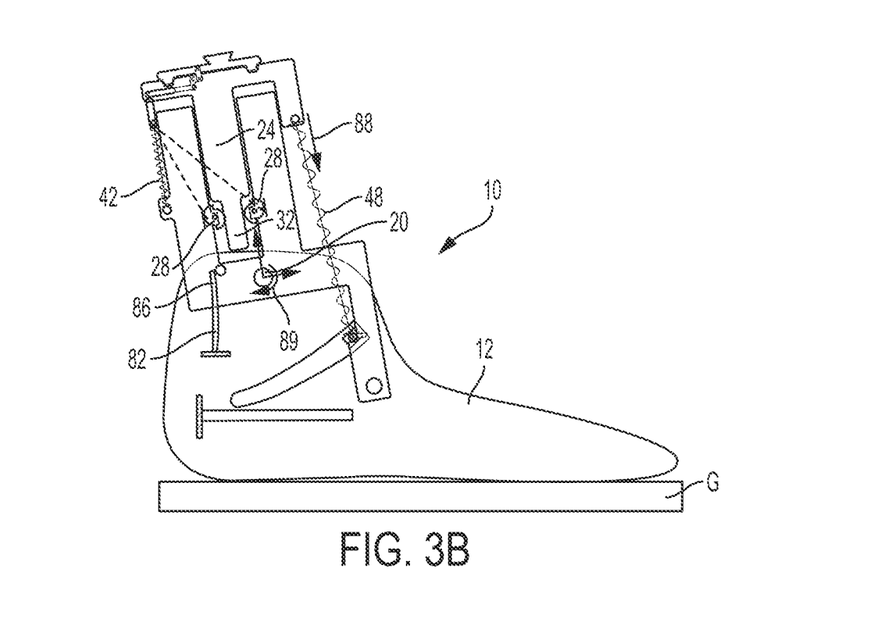

In FIG. 3B, the foot prosthesis 12 is flat against the ground G. The foot prosthesis 12 is lightly loaded as the center of mass of the patient is located directionally behind the ankle joint 20. As the patient continues to move forward, the upper ankle 16 and the lower ankle 18, along with the leg (not depicted) of the patient continue to pivot about the ankle joint 20 in the direction of arrow 89. As the patient's center of mass continues to vertical alignment with the angle joint 20, further translative force is applied in the direction of arrow 88 on the passive ankle prosthesis 10, which further compresses the upper ankle 16 into the lower ankle 18 in the direction of arrow 88. This, in turn, further compresses the sprag release spring 42 and the coupling spring 48, storing energy therein. The rotation of the foot prosthesis 12 into full contact with the ground G further displaces the displacement end 86 of the plantarflexion flexure 82 storing energy therein as well.

Figure 3C:
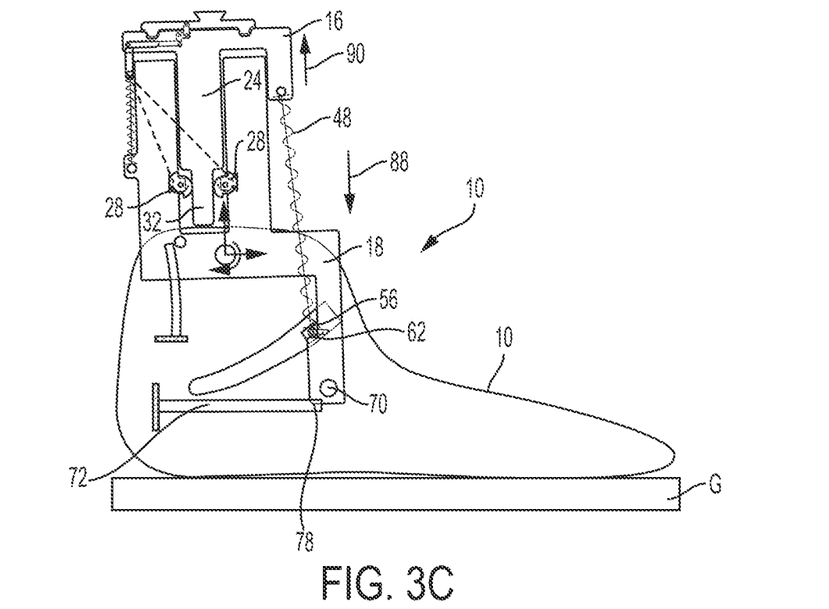

In FIG. 3C the passive ankle prosthesis 10 is fully loaded with the center of mass of the patient vertically above the ankle joint 20. This loads the passive ankle prosthesis 10 with the full weight of the patient. In the fully loaded foot flat condition, the coupling spring 48 is in a fully compressed state, storing the maximum available translative force. In the fully loaded condition, the coupling spring 48 looks to decompress through expansion of the coupling spring 48, exemplarily placing a force in the direction of arrow 88 on the lower ankle 18, by way of engagement between the block 56 at the lower end of the coupling spring 48 with the ledge 62 of the lower ankle 18. The coupling spring 48 exemplarily places a force in the direction of arrow 90 on the upper ankle 16. The sprag release spring 42 also imparts similar expansive forces against the lower ankle 18 and the upper ankle 16. However, as the upper ankle 16 translates in the direction of arrow 88 relative to the lower ankle 18, the ball spline 24, and more specifically, the tongue 32 of the ball spline 24 engages and rotates sprags 28 which frictionally lock the relative positions between the upper ankle 16 and the lower ankle 18, locking the coupling spring 48 in its maximally compressed state. The dorsiflexion contactor 70 begins to engage the displacement end 78 of the dorsiflexion flexure 72. This stores rotative energy in the dorsiflexion flexure 72.

Figure 3D:
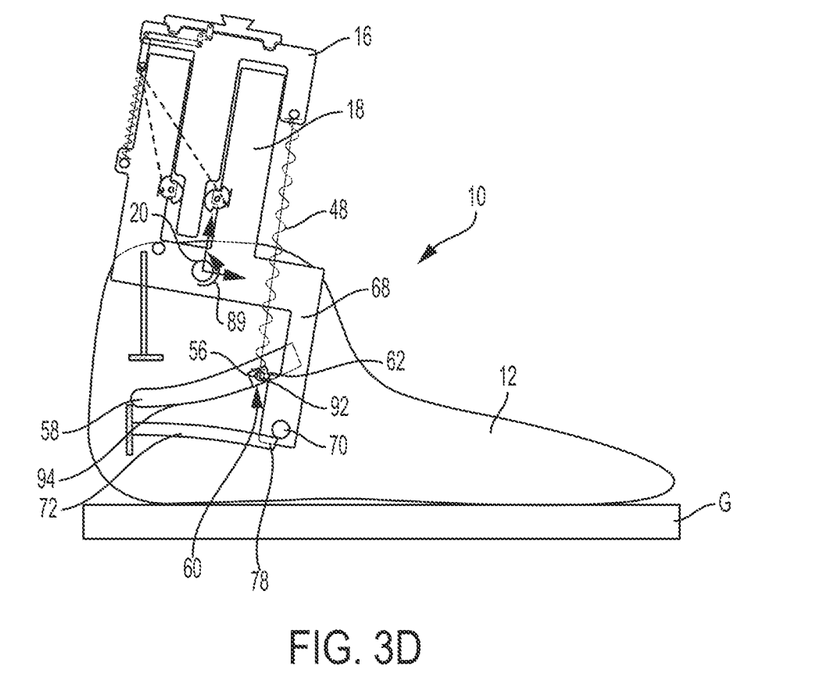

FIG. 3D depicts the passive ankle prosthesis 10 in a condition immediately after maximum dorsiflexion. The leg of the patient as well as the upper ankle 16 and lower ankle 18 now pivot about the ankle joint 20 in the direction of arrow 89, opposite the previous direction of rotation.

The rotation of the upper ankle 16 and the lower ankle 18 about the ankle joint 20 in the direction of arrow 89 moves the lower portion 68 of the lower ankle 18 in the direction away from the ground G.

Additionally, movement of the lower portion 68 away from the ground G similarly moves the ledge 62 in the same direction. The block 58 supported by the ledge 62 moves in this direction as well until a jamming mechanism 60 which includes a sprag 92 engages a lower surface 94 of the channel 58. With the sprag 92 of the jamming mechanism 60 engaged with the foot prosthesis 12 (e.g. lower surface 94 of channel 58), the block 56 is released from engagement with the ledge 62. The block 56, under the expansive force of the coupling spring 48, settles into an equilibrium point within the channel 58, still maintaining the energy stored in the compression of the coupling spring 48, but now the coupling spring 48 places the expansive force between the foot prosthesis 12 and the upper ankle 16. This mechanical coupling between the upper ankle 16 and the foot prosthesis 12 transfers the energy stored in leg deflection into energy that can be released as ankle rotation during the push-off phase.

Figure 3E:
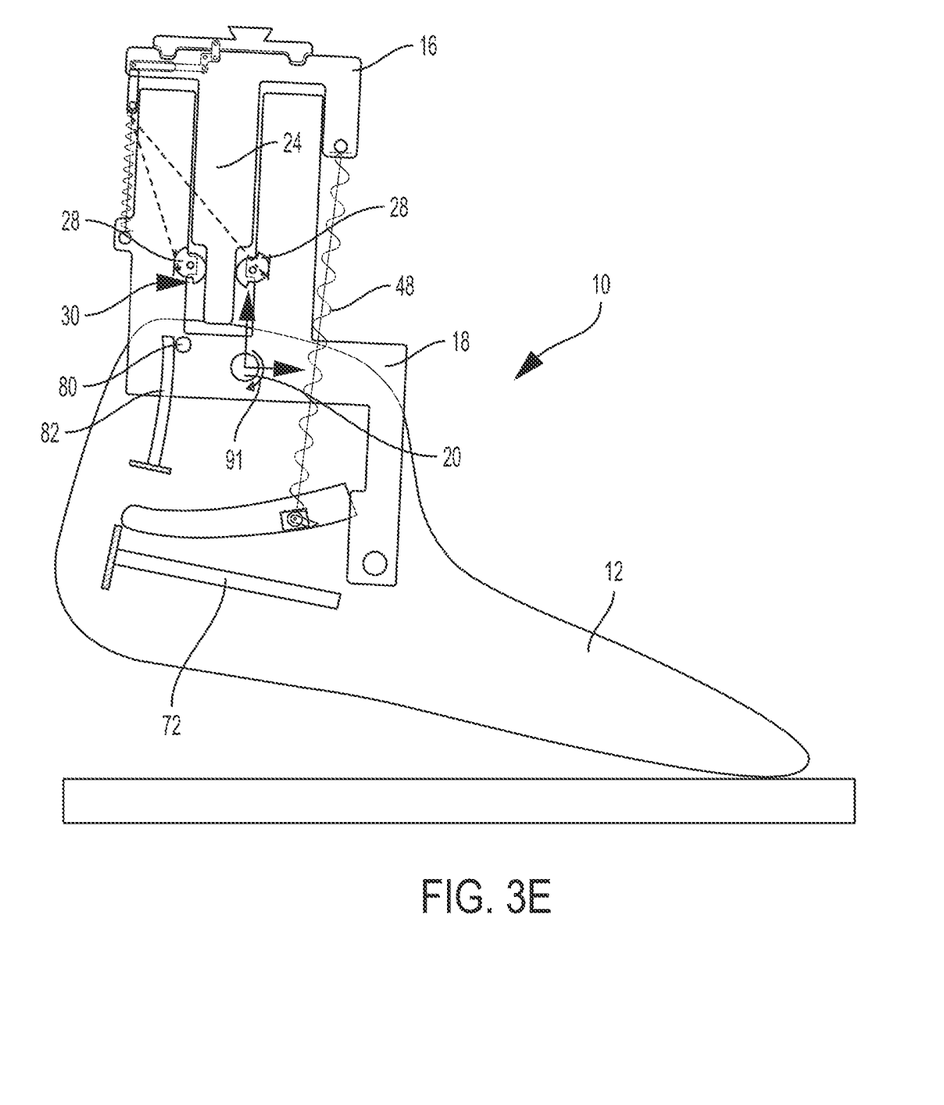

FIG. 3E depicts the passive ankle prosthesis 10 toward the end of powered push-off. During powered push-off the coupling spring 48 and the dorsiflexion flexure 72 release the energy stored within these springs to generate torque about the ankle joint 20 on the foot in the direction of arrow 91. This propels the walker forward. As powered push-off continues, the rotation of the lower ankle 18 about the ankle joint 20 engages the plantarflexion flexure 82 with the plantarflexion contactor 80 to store some rotational energy in the plantarflexion flexure 82. Just prior to toe off, as depicted in FIG. 3E, the coupling spring 48 may not have released all of the energy stored therein as the jamming mechanism 30 locks the ball spline 24 with the sprags 28 which prevents release and upward movement of the upper ankle 16 similarly preventing further upward movement of the upper ankle 16. Therefore, some energy may remain stored in the coupling spring 48. In exemplary embodiments, although not depicted in FIG. 3E, energy may similarly remain stored in the dorsiflexion flexure 72.

Figure 3F:
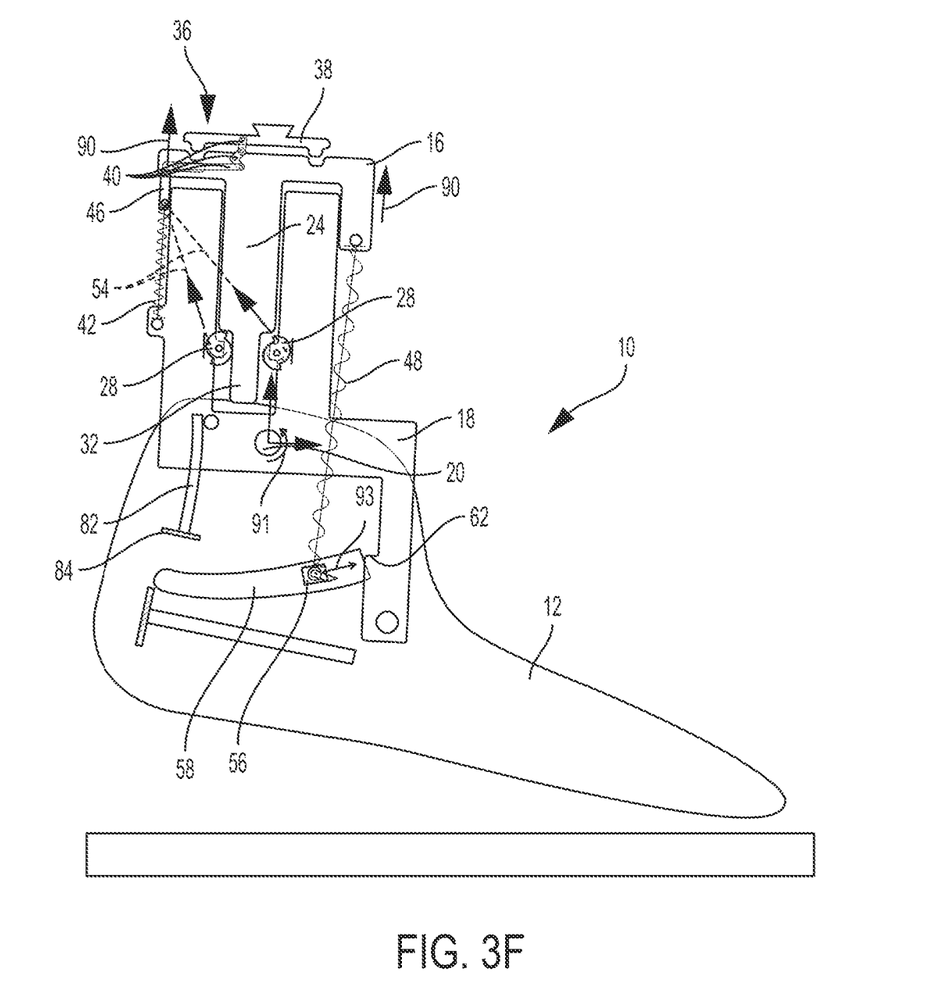

FIG. 3F depicts the passive ankle prosthesis during toe-off and a swing phase reset. Once the foot breaks contact with the ground (toe oft), the force provided by the leg to move the foot forward causes the pyramid adaptor 38 to be moved upward relative to the upper ankle 16, at least partially separating from the upper ankle 16. This operates the sprag release mechanism 36 by moving links 40, out of engagement with the spring adaptor 46 of the sprag release spring 42. The energy stored in the sprag release spring 42 moves the spring adaptor 46 upwards in the direction of arrow 90. As the spring adaptor 46 moves upward in the direction of arrow 90, the sprag wires 54 connected between the spring adaptor 46 and the sprags 28 place a releasing force on the sprags 28. The sprags 28 rotate, disengaging the sprags 28 from the tongue 32 of the ball spline shaft 34. With the sprags 28 no longer locking against the ball spline 24, the upper ankle 16 is freed for movement in the direction of arrow 90. The remaining energy stored in the coupling spring 48 is released to move the upper ankle 16 in the direction of arrow 90 relative to the lower ankle 18.

The energy stored in the plantarflexion flexure 82 is released through fixed end 84 to rotate the foot prosthesis 12 about the ankle joint 20 lifting the foot 12 and toe. With the energy in the coupling spring 48 released, the block 56 is free to move within the channel 58 and the rotation of the foot prosthesis 12 about the ankle joint 20 in the direction of arrow 91 moves the block 56 within the channel 58 in the direction of arrow 93. This movement of the foot prosthesis 12 and the block 56 reseats the block 56 on the ledge 62 of the lower ankle 18. In this manner, the passive ankle prosthesis is reset to an unloaded position as depicted in FIG. 1 and ready for a subsequent step by the patient.

Figure 5:
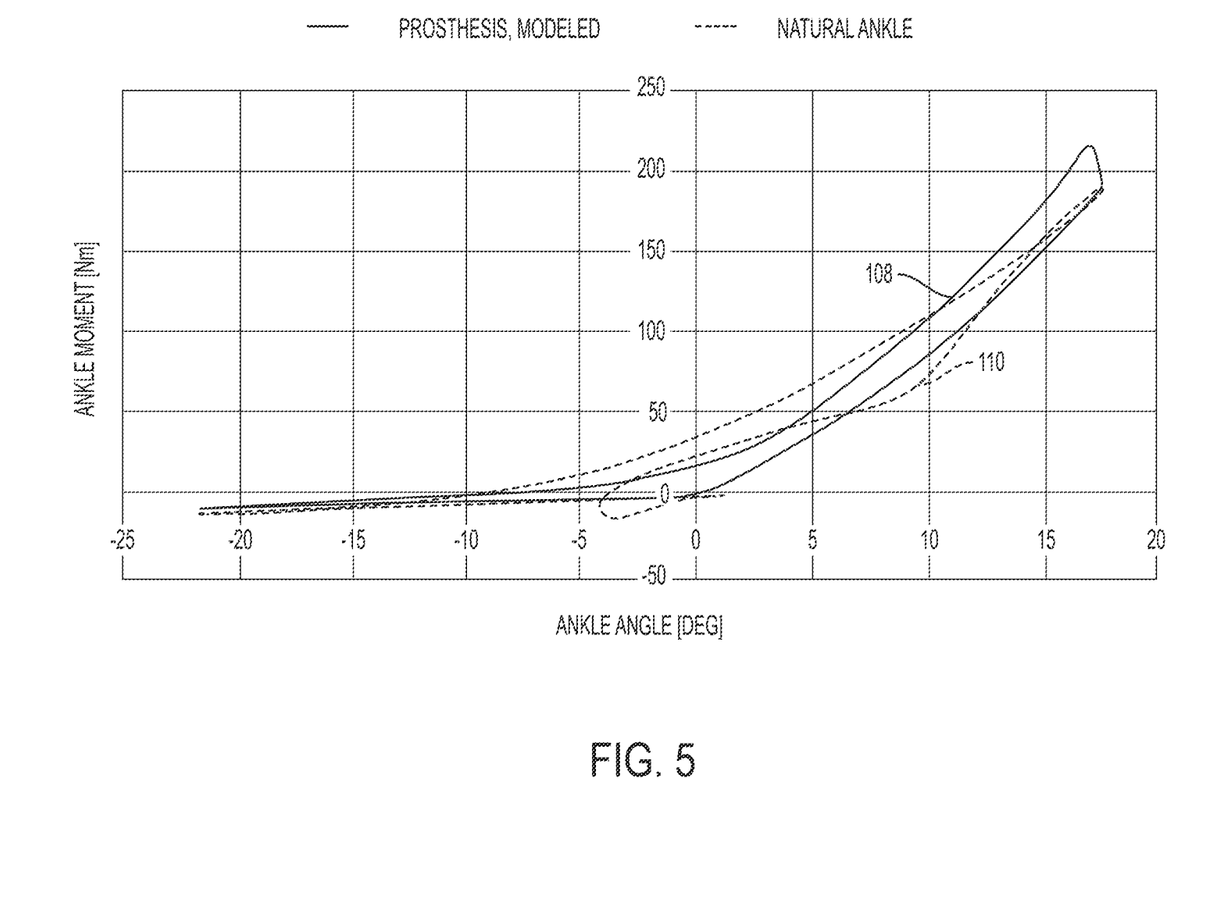
FIG. 5 is a graph that presents exemplary experimental data of ankle moment (Nm) versus ankle angle for a modeled passive ankle and a human test subject.

FIG. 5 is a graph that depicts exemplary data of M(θ) between an exemplary embodiment of the passive ankle prosthesis 108 and the human test subject 110. As can be seen from the graph of FIG. 5, the work output of the passive ankle prosthesis closely models that of a natural ankle.

In the embodiments of the passive ankle prosthesis and method of operation as described herein, passively-obtained energy return increases with increase in walking speed. Since increased walking speed produces greater force, this increased forced is captured, stored, and released by embodiments disclosed herein, thus producing a passive ankle prosthesis in which the work output increases with increase in walking speed to thereby passively aid walking with ankle work return over a wider range of walking speeds.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ankle prosthesis, comprising:
 a foot prosthesis;
 a lower ankle pivotably secured to the foot prosthesis at an ankle joint;
 an upper ankle connected to the lower ankle in a manner that permits vertical movement of the upper ankle relative to the lower ankle; and
 a coupling spring biased in an extended condition, the coupling spring connected at a first end to the upper ankle, a second end of the coupling spring movable in a first condition engaged to the lower ankle and in a second condition engaged to the foot prosthesis, whereby energy is stored in compression of the coupling spring when the coupling spring is in the first condition and energy is released from the coupling spring when the coupling spring is in the second condition,
 wherein the upper ankle comprises a ball spline telescopically movable within the lower ankle, and the ankle prosthesis further comprises:
 at least one sprag movably secured to the lower ankle and engagable with the ball spline shaft, wherein operable engagement of the at least one sprag with the ball spline shaft permits movement of the upper ankle towards the lower ankle, and prevents movement of the upper ankle away from the lower ankle.

2. The ankle prosthesis of claim 1, further comprising:
a sprag release spring secured a first end to the lower ankle and a second end of the sprag release spring is selectively engaged with the upper ankle such that, when the second end of the sprag release spring is engaged with the upper ankle, translation of the upper ankle towards the lower ankle stores energy in compression of the sprag release spring; and
at least one sprag wire secured between the second end of the sprag release spring and the at least one sprag, wherein disengagement between the second end of the sprag release spring and the upper ankle, imparts a rotative force on the at least one sprag through the at least one sprag wire to disengage the at least one sprag from the ball spline of the upper ankle.

3. An ankle prosthesis, comprising:
a foot prosthesis;
a lower ankle pivotably secured to the foot prosthesis at an ankle joint;
an upper ankle connected to the lower ankle in a manner that permits vertical movement of the upper ankle relative to the lower ankle;
a coupling spring biased in an extended condition, the coupling spring connected at a first end to the upper ankle, a second end of the coupling spring movable in a first condition engaged to the lower ankle and in a second condition engaged to the foot prosthesis, whereby energy is stored in compression of the coupling spring when the coupling spring is in the first condition and energy is released from the coupling spring when the coupling spring is in the second condition;
a pyramid adaptor movably connected to the upper ankle; and
a sprag release mechanism comprising a plurality of links, at least one link of the plurality of links provides the selective engagement between the second end of the sprag release spring and the upper ankle; and wherein movement of the pyramid adaptor away from the upper ankle disengages the at least one link and the upper ankle from the sprag release spring.

4. An ankle prosthesis, comprising:
a foot prosthesis;
a lower ankle pivotably secured to the foot prosthesis at an ankle joint, the lower ankle comprising a ledge;
an upper ankle connected to the lower ankle in a manner that permits vertical movement of the upper ankle relative to the lower ankle;
a coupling spring biased in an extended condition, the coupling spring connected at a first end to the upper ankle, a second end of the coupling spring movable in a first condition engaged to the lower ankle and in a second condition engaged to the foot prosthesis, whereby energy is stored in compression of the coupling spring when the coupling spring is in the first condition and energy is released from the coupling spring when the coupling spring is in the second condition;
a block at the second end of the coupling spring, wherein the block engages the ledge of the lower ankle when the coupling spring is in the first condition; and
a jamming mechanism connected to the block, wherein the jamming mechanism engages the foot prosthesis to move the block from engagement with the ledge of the lower ankle in the first condition of the coupling spring to engagement with the foot prosthesis in the second condition of the coupling spring.

5. The ankle prosthesis of claim 4, wherein during a swing phase, movement of the upper ankle lifting the second end of the coupling spring and rotation of the foot prosthesis about the ankle joint engages the block with the ledge of the lower ankle to reset the ankle prosthesis.

6. The ankle prosthesis of claim 4, further comprising at least one toe prosthesis movably secured to the foot prosthesis.

7. An ankle prosthesis, comprising:
a foot prosthesis;
a lower ankle pivotably secured to the foot prosthesis at an ankle joint;
an upper ankle connected to the lower ankle in a manner that permits vertical movement of the upper ankle relative to the lower ankle;
a coupling spring biased in an extended condition, the coupling spring connected at a first end to the upper ankle, a second end of the coupling spring movable in a first condition engaged to the lower ankle and in a second condition engaged to the foot prosthesis, whereby energy is stored in compression of the coupling spring when the coupling spring is in the first condition and energy is released from the coupling spring when the coupling spring is in the second condition;
a dorsiflexion contactor secured to the lower ankle; and
a dorsiflexion flexure secured to the foot prosthesis, wherein the dorsiflexion contactor is configured to selectively engage a displacement end of the dorsiflexion flexure to store energy in the dorsiflexion flexure from rotation decreasing an angle between the foot prosthesis and the lower ankle about the ankle joint.

8. The ankle prosthesis of claim 7 wherein the dorsiflexion contactor is secured to a lower portion of the lower ankle and the dorsiflexion flexure is fixed to the foot prosthesis at a fixed end of the dorsiflexion flexure and the dorsiflexion flexure in an unloaded condition extends generally parallel to the foot prosthesis.

9. The ankle prosthesis of claim 7, wherein dorsiflexion flexure is bifurcated into a first projection and a second projection, the dorsiflexion contactor is a first dorsiflexion contactor, the lower ankle further comprises a second dorsiflexion contactor, and the first and second dorsiflexion contactors selectively engage the first and second projections.

10. The ankle prosthesis of claim 7, wherein the dorsiflexion flexure releases energy stored therein to increase an angle between the foot prosthesis and the lower ankle about the ankle joint.

11. The ankle prosthesis of claim 7, wherein in a loading phase, a translative input force is stored in the coupling spring and rotative input force is stored in the dorsiflexion flexure.

12. The ankle prosthesis of claim 11, wherein in a push-off phase the energy stored in the coupling spring and the dorsiflexion flexure is released to propel forward a patient using the ankle prosthesis.

13. An ankle prosthesis, comprising:
a foot prosthesis;
a lower ankle pivotably secured to the foot prosthesis at an ankle joint;
an upper ankle connected to the lower ankle in a manner that permits vertical movement of the upper ankle relative to the lower ankle;
a coupling spring biased in an extended condition, the coupling spring connected at a first end to the upper ankle, a second end of the coupling spring movable in a first condition engaged to the lower ankle and in a second condition engaged to the foot prosthesis, whereby energy is stored in compression of the coupling spring when the coupling spring is in the first condition and energy is released from the coupling spring when the coupling spring is in the second condition;

a plantarflexion contactor secured to the lower ankle; and a plantarflexion flexure secured to the foot prosthesis, wherein the plantarflexion contactor is configured to selectively engage a displacement end of the plantarflexion flexure to store energy in the plantarflexion flexure from rotation increasing an angle between the foot prosthesis and the lower ankle about the ankle joint.

14. The ankle prosthesis of claim 13, wherein the plantarflexion flexure releases energy stored therein to decrease an angle between the foot prosthesis and the lower ankle about the ankle joint.

15. The ankle prosthesis of claim 14, wherein in a loading phase, the plantarflexion flexure releases energy stored therein to assist movement of the upper ankle and the lower ankle into vertical alignment on the ankle joint and in a toe-off phase, the plantarflexion flexure releases energy stored therein to lift the foot prosthesis during a swing phase.

16. A method of passive energy return in the ankle prosthesis of claim 4, comprising:
    operating the coupling spring in the first condition with the second end of the coupling spring engaged with the lower ankle;
    receiving a translational force on the upper ankle;
    storing energy in compression of the coupling spring;
    operating the coupling spring in the second condition with the second end of the coupling spring engaged with the foot prosthesis;
    releasing energy stored in the coupling spring to aid rotation of the foot prosthesis relative to the upper ankle about the ankle joint.

17. The method of claim 16 wherein energy return increases with walking speed.

* * * * *